United States Patent [19]

Bantick et al.

[11] 4,213,903

[45] Jul. 22, 1980

[54] BASIC AMINO ACID SALTS OF CHROMONES

[75] Inventors: John R. Bantick; David N. Hardern; Thomas B. Lee, all of Loughborough, England

[73] Assignee: Fisons Limited, London, England

[21] Appl. No.: 869,653

[22] Filed: Jan. 16, 1978

[30] Foreign Application Priority Data

Jan. 26, 1977 [GB] United Kingdom ................ 3061/77

[51] Int. Cl.² .................. C07D 257/04; C07D 311/22
[52] U.S. Cl. ................................. 548/250; 260/345.2; 424/269; 424/283
[58] Field of Search ......................... 260/345.2, 308 D

[56] References Cited

U.S. PATENT DOCUMENTS

| | | | |
|---|---|---|---|
| 3,804,880 | 4/1974 | Bergstrom et al. | 260/501.17 |
| 3,879,411 | 4/1975 | Cairns et al. | 260/308 D |
| 4,029,802 | 6/1977 | Augustein et al. | 260/308 D |

FOREIGN PATENT DOCUMENTS 1132287 10/1968 United Kingdom ............. 260/345.7 R

OTHER PUBLICATIONS

Augstein et al, Chem Abstract, 78, 124,444c (1973) (Abstract of German Offlegungsschrift 2,237,100).
Pigman, The Carbohydrates, pp. 475–476 (1957).

*Primary Examiner*—Nicky Chan
*Attorney, Agent, or Firm*—Merriam, Marshall & Bicknell

[57] ABSTRACT

The present invention relates to salts with basic amino sugars or basic amino acids of certain 2-carboxy or 2-tetrazolo-chromones.

5 Claims, No Drawings

BASIC AMINO ACID SALTS OF CHROMONES

This invention concerns new compounds, processes for their preparation, and compositions containing them.

The new compounds of the present invention are the salts with basic aminosugars or basic amino acids (i.e. those having more than one amino group) of the compounds of formula I:

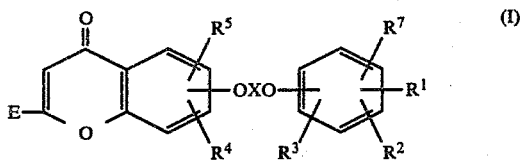

wherein $R^1$, $R^2$, $R^3$, $R^4$, $R^5$ and $R^7$ may be the same or different, and are hydrogen, hydroxy, alkoxy, alkoxy substituted by phenyl, carboxylic acyl, amino, acylamino, alkenyl, halogen or alkyl, provided that at least one of $R^1$, $R^2$, $R^3$ and $R^7$ are other than hydrogen and hydroxy, or an adjacent pair of $R^1$, $R^2$, $R^3$ and $R^7$ either represent hydroxyl and a 3-(N,N-dialkylamino)acryloyl radical or together represent a chain

—COCH=CH—O—,

X is a hydrocarbon chain containing from 2 to 10 carbon atoms and optionally substituted by a hydroxy group, and E is a carboxy group or a tetrazole group.

The compounds of the present invention possess pharmacological properties. In particular, the compounds are antagonists of the slow-reacting substance of anaphylaxis (SRS-A), or its pathological effects, as is indicated by their activity in the test set out in Example A. The compounds also antagonise the effects of SRS-A obtained during antigen challenge of sensitized human chopped lung on isolated guinea pig ileum as described in Example A. The compounds also have the same utility at the same dosages as the compounds of Dutch Patent Specification No. 68,11740.

The compounds are thus indicated for use in the treatment of disorders in which SRS-A is a factor, for example skin afflictions, hay fever and obstructive airway diseases, e.g. asthma.

For the above-mentioned uses, the dosage administered will, of course, vary depending upon the compound employed mode of administration and treatment desired. However, in general satisfactory results are obtained when administered at a daily dosage of from about 1 milligram to about 10 milligrams per kilogram of animal body weight, preferably given in divided doses 2 to 4 times a day or in sustained release form. For the larger mammals, the total daily dosage is in the range of from about 50 milligrams to about 700 milligrams, and dosage forms suitable for administration comprise from about 12 milligrams to about 350 milligrams of the compound admixed with a solid or liquid pharmaceutical carrier or diluent. The compounds may be administered during or before the attack of the disorder to be treated.

The compounds may be administered in association with a pharmaceutically acceptable adjuvant, diluent or carrier, the composition used depending on many factors including the disorder to be treated. The compounds may be administered parenterally by inhalation or topically, preferably by inhalation. For inhalation they are desirably presented either as aqueous solutions or as powders. The powders may conveniently contain lactose as the carrier material.

It is preferred that no more than 3 of $R^1$, $R^2$, $R^3$ and $R^7$ are other than hydrogen. Preferred values of $R^1$, $R^2$, $R^3$, $R^4$, $R^5$ and $R^7$ are hydrogen, hydroxy, lower alkoxy, lower alkoxy substituted by phenyl, lower acyl (e.g. lower alkanoyl or lower alkenoyl), or lower alkenoyl substituted by an amino or a mono- or di-loweralkyl amino group, amino, lower acyl amino (e.g. lower alkanoylamino), lower alkenyl, halogen (i.e. chlorine, bromine or iodine) or lower alkyl.

Specific examples of values of $R^1$, $R^2$, $R^3$, $R^4$, $R^5$ and $R^7$ are hydrogen, hydroxy, methoxy, benzyloxy, acetyl, dimethylaminoacryloyl, amino, acetylamino, allyl, methyl, ethyl, n-propyl and n-butyl.

Preferred compounds of formula I are those in which $R^5$ is hydrogen, $R^4$ is hydrogen, n-propyl or allyl, $R^7$ is hydrogen, $R^1$ is hydrogen, propyl or allyl, $R^2$ is hydroxy and $R^3$ is acetyl.

The group X is preferably a straight chain alkylene group containing, for example, from 3 to 7 carbon atoms and optionally substituted by a hydroxy group.

The aminosugar and amino acid salts of the following compounds are specifically preferred:

7-[5-(4-acetyl-3-hydroxyphenoxy)pentyloxy]-4-oxo-4H-1-benzopyran-2-carboxylic acid, 8-Allyl-7-[5-(4-acetyl-2-allyl-3-hydroxyphenoxy)pentyloxy]-4-oxo-4H-1-benzopyran-2-carboxylic acid, 8-Allyl-7-[5-(4-acetylphenoxy)pentyloxy]-4-oxo-4H-1-benzopyran-2-carboxylic acid, 8-Allyl-7-[5-(2-acetyl-3-hydroxyphenoxy)pentyloxy]-4-oxo-4H-1-benzopyran-2-carboxylic acid, 8-Allyl-7-[5-(4-acetylaminophenoxy)pentyloxy]-4-oxo-4H-1-benzopyran-2-carboxylic acid, 7-[5-(4-Acetylphenoxy)pentyloxy]-4-oxo-4H-1-benzopyran-2-carboxylic acid, 7-[5-(3-Methoxyphenoxy)pentyloxy]-4-oxo-4H-1-benzopyran-2-carboxylic acid, 7-[5-(3-Benzyloxyphenoxy)pentyloxy]-4-oxo-4H-1-benzopyran-2-carboxylic acid, 7-[5-(2-Acetyl-4-allyl-3-hydroxyphenoxy)pentyloxy]-4-oxo-4H-1-benzopyran-2-carboxylic acid, 4-Oxo-7-[5-(2-propylphenoxy)pentyloxy]-4H-1-benzopyran-2-carboxylic acid, 7-[5-(2-t-Butylphenoxy)pentyloxy]-4-oxo-4H-1-benzopyran-2-carboxylic acid, 8-Allyl-7-[3-(4-acetyl-2-allyl-3-hydroxyphenoxy)-2-hydroxypropoxy]-4-oxo-4H-1-benzopyran-2-carboxylic acid, 7-[3-(4-Acetyl-3-hydroxyphenoxy)-2-hydroxypropoxy]-4-oxo-4H-1-benzopyran-2-carboxylic acid, 8-Allyl-7-[3-(4-acetyl-3-hydroxyphenoxy)-2-hydroxypropoxy]-4-oxo-4H-1-bnzopyran-2-carboxylic acid, 7-[3-(4-Acetyl-3-hydroxy-2-allylphenoxy)-2-hydroxypropoxy]-4-oxo-4H-1-benzopyran-2-carboxylic acid, 8-Propyl-7-[3-(4-acetyl-3-hydroxy-2-n-propylphenoxy)-2-hydroxypropoxy]-4-oxo-4H-1-benzopyran-2-carboxylic acid, 4-Oxo-8-propyl-7-[3-(2-propylphenoxy)-2-hydroxypropoxy]-4H-1-benzopyran-2-carboxylic acid, 4-Oxo-7-[3-(2-propylphenoxy)-2-hydroxypropoxy]-4H-1-benzopyran-2-carboxylic acid, 7-[3-(2-Allylphenoxy)-2-hydroxypropoxy]-4-oxo-4H-1-benzopyran-2-carboxylic acid, 7-[3-(4-Acetyl-3-hydroxy-2-propylphenoxy)-2-hydroxypropoxy]-4-oxo-4H-1-benzopyran-2-carboxylic acid, 7-[3-(4-Acetyl-3-hydroxy-2-propylphenoxy)-2-hydroxypropoxy]-4-oxo-6-propyl-4H-1-benzopyran-2-carboxylic acid, 4-Oxo-6-propyl-7-[3-(2-propylphenoxy)-2-hydroxypropoxy]-4H-1-benzopyran-2-carboxylic acid, 7-[2-Hydroxy-3-(2,4-dimethylphenoxy)propoxy]-4-oxo-4H-1-benzopyran-2-carboxylic acid, 7-[3-(2,4-Di-t-butylphenoxy)-2-hydroxypropoxy]-4-oxo-4H-1-benzopyran-2-carboxylic acid, 7-(3-[2-t-Butylphenoxy]-2-hydroxypropoxy)-4-oxo-4H-1-benzopyran-2-carboxylic acid, 7-[5-(4-Oxo-4H-1-benzopyran-7-yloxy)pentyloxy]-4-oxo-4H-1-benzopyran-2-carboxylic acid, 7-[3-(4-Oxo-4H-1-benzopyran-7-yloxy)-2-hydroxypropoxy]-4-oxo-4H-1-benzopyran-2-carboxylic acid, 7-[3-(4-Acetyl-3-hydroxy-2-propylphenoxy)propoxy]-4-oxo8-propyl-4H-1-benzopyran-2-carboxylic acid, 4-Oxo-8-propyl-7-[3-(2-propylphenoxy)propoxy]-4H-1-benzopyran-2-carboxylic acid, 4-Oxo-6-propyl-7-[3-(2-propylphenoxy)propoxy]-4H-1-benzopyran-2-carboxylic acid, 8-(3-[2-t-Butylphenoxy]-2-hydroxypropoxy)-4-oxo-4-H-1-benzopyran-2-carboxylic acid, 8-[2-Hydroxy-3-(2-iodophenoxy)propoxy]-4-oxo-4-H-1-benzopyran-2-carboxylic acid, 8-[3-(2-n-butylphenoxy)-2-hydroxypropoxy]-4-oxo-4H-1-benzopyran-2-carboxylic acid, 8-[2-Hydroxy-3-(2-propylphenoxy)propoxy]-4-oxo-4H-1-benzopyran-2-carboxylic acid, 8-(3-[2-n-butylphenoxy]-propoxy)-4-oxo-4H-1-benzopyran-2-carboxylic acid, 4-Oxo-8-[7-(2-n-propylphenoxy)heptyloxy]-4H-1-benzopyran-2-carboxylic acid, 4-Oxo-7-[7-(2-n-propylphenoxy)heptyloxy]-4H-1-benzopyran-2-carboxylic acid, 6-[2-Hydroxy-3-(2-propylphenoxy)propoxy]-4-oxo-4H-1-benzopyran-2-carboxylic acid, 5-[2-Hydroxy-3-(2-propylphenoxy)propoxy]-4-oxo-4H-1-benzopyran-2-carboxylic acid, 4-Oxo-7-(3-[2-propylphenoxy]propoxy)-4-H-1-benzopyran-2-benzopyran-2-carboxylic acid, 5-(4-Oxo-7-[3-(2-propylphenoxy)-propoxy]-4H-1-benzopyran-2-yl)tetrazole, 8-Ethyl-4-oxo-7-(3-[2-propylphenoxy]propoxy)-4H-1-benzopyran-2-carboxylic acid, 5-(3-[2-Acetyl-3-hydroxyphenoxy]-2-hydroxypropoxy)-4-oxo-4H-1-benzopyran-2-carboxylic acid, 5-(3-[4-oxo-1-benzopyran-5-yloxy]-2-hydroxypropoxy)-4-oxo-4H-1-benzopyran-2-carboxylic acid, and 5-(3-[2-(3-dimethylaminocryloyl)-3-hydroxyphenoxy]-2-hydroxypropoxy)-4-oxo-4H-1-benzopyran-2-carboxylic acid, 8-propyl-7-[3-(4-acetyl-3-hydroxy-2-propyl-phenoxy)-2-hydroxypropoxy]-4-oxo-4H-1-benzopyran-2-carboxylic acid.

In this specification and in the claims 'lower' is used to mean a group containing up to 6, i.e. 1 to 6, or, as necessary, from 2 to 6 or 3 to 6 carbon atoms.

The preferred amino acids which form the salts are lysine, ornithine and arginine or an N-alkyl, especially an N-methyl, derivative thereof. The preferred aminosugars are glucamine, N-methylglucamine and glucosamine. The amino sugar or amino acid employed may be in optically active or racemic form.

Particularly preferred are the salts, particularly the ornithine and and, especially, the lysine salt of 8-propyl-7-[3-(4-acetyl-3-hydroxy-2-propyl-phenoxy)-2-hydroxypropoxy]-4-oxo-4H-1-benzopyran-2-carboxylic acid.

The amino acid and aminosugar salts of the present invention are surprisingly more soluble than the corresponding alkali-metal salts. The increased solubility permits, inter alia, the administration of higher concentrations of active ingredient to the patient. Moreover, the salts of the present invention overcome a further problem associated with the use of the corresponding alkali-metal salts namely that of cloudiness of solutions thereof which develops when the solutions have been left to stand for some time. Besides leading to an unacceptable appearance the cloudiness which is caused by precipitation of the less soluble calcium and magnesium salts can lead to blockage in aerosol dispensers and nebulisers. Although the cloudiness can be removed by filtration, it develops only very slowly and thus may reappear even after filtration. With the present salts the precipitation occurs immediately and filtration renders the solutions permanently clear.

The invention also provides a process for the preparation of an aminosugar or amino acid salt of a compound of formula I which process comprises reacting a compound of formula I with the desired basic aminosugar or basic amino acid.

For parenteral use it is necessary for the formulation of any compound to be sterile and pyrogen-free and this is also desirable where it is to be used by inhalation. Normally, this can be achieved simply by making up, using pyrogen-free components, a solution or suspension of the compound, which is then sterilised, usually by autoclaving. However in the case of the benzopyran salts of this invention, the solutions are unstable even at ambient temperature and decomposition occurs above about 40° C., such a temperature being too low to effect sterilisation.

We have now developed a method by which the above-mentioned benzopyran salts may be prepared in sterile, pyrogen-free form.

Accordingly, in another aspect, this invention provides a process for the preparation of a pharmaceutically-acceptable basic aminosugar or basic amino acid salt of a compound of formula I in sterile, pyrogen-free form, which comprises washing a sample of the compound of formula I with pyrogen-free distilled water, optionally (and preferably) suspending the washed material in pyrogen-free distilled water, adding to the acid or suspension thereof a solution of the basic aminosugar or amino acid in pyrogen-free distilled water, removing any insoluble matter, sterile filtering the resulting solution, optionally (and preferably) allowing the filtrate to stand followed by further sterile filtration, and freeze-drying under sterile conditions.

The base is desirably added to the acid or suspension thereof in a stoichiometric amount or, failing that, in such an amount that a slight excess of the acid remains. If, as preferred, the formed solution of the desired salt is allowed to stand, insoluble salts of the compound of formula I with metal cations present precipitate out and may readily be removed by the sterile filtration step.

The freeze-drying step is desirably effected in sterile, pyrogen-free ampoules, which are sealed aseptically and from which the benzopyran salt may be released as required and dissolved in pyrogen-free distilled water immediately prior to use. The freeze-drying step is preferably effected as soon as possible after the last sterile filtration.

At all stages, the temperature is preferably kept below 40° C., and more preferably below 25° C.

The pyrogen-free distilled water preferably contains less than 2 ppm zinc and less than 0.04 ppm magnesium.

The invention is further described, though only by way of illustration, in the following Examples, in which all 'parts' are by weight.

EXAMPLE A

The procedure set out below is used to assess the effectiveness of a compound in antagonizing SRS-A. The test makes use of the agonist (contractile) effect of SRS-A on isolated guinea-pig ileum.

A satisfactory preparation of SRS-A can be obtained from egg albumen sensitised guinea pigs. Three weeks after sensitisation, the lungs from such guinea-pigs are removed, perfused free of blood, and chopped. Samples of washed, chopped lung are then challenged with egg albumen (antigen) solution. The supernatants collected 15 minutes after addition of antigen contain histamine and SRS-A and can be used, in the presence of an antihistamine, to induce effects due to SRS-A.

An isolated section of the terminal portion of a guinea-pig ileum is suspended in Tyrode solution, which contains atropine sulphate $10^{-6}$ M (700 g/liter) and mepyramine maleate $10^{-6}$ M ((400 g/liter). Atropine sulphate is included to reduce the spontaneous activity of the ileum preparation and to exclude the effects of possible cholinergic agents. Mepyramine maleate is included to exclude the effects of histamine. The composition of the Tyrode solution in g/l distilled water is NaCl 8.0, KCl 0.2, $CaCl_2$ 0.2, $MgCl_2$ 0.1, $NaHCO_3$ 1.0, $NaH_2PO_4 2H_2O$ 0.05 and dextrose 1.0. A 2 ml organ bath is preferred for economy of SRS-A, the tension on the tissue should be about 600 mg and the bathing temperature 37° C.

A dose of unpurified SRS-A is selected which produced similar repetitive submaximal contractions of the ileum. Each contraction is recorded for 90 seconds when the tissue is washed to allow relaxation. Five minutes is allowed between doses of SRS-A.

The compound under test is added to the organ bath 30 seconds before a dose of SRS-A. A range of concentrations of the compound is chosen to give a log concentration/inhibitory response graph. From this graph, the concentration of compound which would inhibit the ileum contraction to SRS-A by 50% ($IC_{50}$) is determined.

EXAMPLE 1

7-[3-(4-Acetyl-3-hydroxy-2-propylphenoxy)-2-hydroxypropoxy]-4-oxo-8-propyl-4H-1-benzopyran-2-carboxylic acid (±) lysine salt A solution of 10.5 parts of 7-[3-(4-acetyl-3-hydroxy-2-propylphenoxy)-2-hydroxypropoxy]-4-oxo-8-propyl-4H-1-benzopyran-2-carboxylic acid and 2.92 parts of (±)-lysine in 500 parts of distilled water was freeze-dried to give 12.0 parts of colourless salt.

Analysis: Found: C, 61.0; H, 7.1; N, 4.2% $C_{33}H_{44}N_2O_{11}$ requires: C, 61.4; H, 6.8; N, 4.3%

EXAMPLE 2

7-[3-(4-Acetyl-3-hydroxy-2-propylphenoxy)-2-hydroxypropoxy]-4-oxo-8-propyl-4H-1-benzopyran-2-carboxylic acid L-lysine salt 7-(3-(4-Acetyl-3-hydroxy-2-propylphenoxy)-2-hydroxypropoxy)-4-oxo-8-propyl-4H-1-benzopyran-2-carboxylic acid (367 g) was washed with copious quantities (20 l) of pyrogen-free distilled water, and was then suspended in further pyrogen-free distilled water (9000 ml). A solution of L-lysine (100 g) in pyrogen-free distilled water (500 ml) was then added with stirring. Stirring was continued until solution of the suspended material was effected. Any insoluble material remaining was removed by sterile filtration and the resulting solution was then allowed to stand for 16 hours in a sterile environment, and was then sterile-filtered through a $0.22\mu$ membrane filter directly into sterile pyrogen-free ampoules. The solution was then freeze-dried immediately in a sterile area, and the ampoules were sealed on completion of the freeze-drying process, using aseptic techniques.

EXAMPLE 3

Salts of 8-propyl-7-[3-(4-acetyl-3-hydroxy-2-n-propyl-phenoxy)-2-hydroxypropoxy]-4-oxo-4H-1-benzopyran-2-carboxylic acid were prepared by reaction of the acid as in Example 1 respectively with ornithine, arginine, glucamine, N-methyl-glucamine and glucosamine.

EXAMPLE 4

By the method of Example 2 are prepared the L-lysine salts of the following compounds which, together with the acid of formula I employed as starting material in that Example, represent a preferred group of compounds:

8-allyl-7-[5-(2-acetyl-3-hydroxyphenoxy)pentyloxy]-4-oxo-4H-1-benzopyran-2-carboxylic acid;

8-allyl-7-[3-(4-acetyl-2-allyl-3-hydroxyphenoxy)-2-hydroxy-propoxy]-4-oxo-4H-1-benzopyran-2-carboxylic acid;

4-oxo-8-propyl-7-[3-(2-propylphenoxy)-2-hydroxypropoxy]-4H-1-benzopyran-2-carboxylic acid;

7-[3-(4-acetyl-3-hydroxy-2-propylphenoxy)-2-hydroxypropoxy]-4-oxo-4H-1-benzopyran-2-carboxylic acid; and 7-[3-(4-acetyl-3-hydroxy-2-propylphenoxy)propoxy]-4-oxo-8-propyl-4H-1-benzopyran-2-carboxylic acid.

We claim:

1. A salt with a basic amino acid selected from the group consisting of lysine, arginine, ornithine, and the N-methyl derivatives of lysine, arginine, and ornithine, of a compound of the formula:

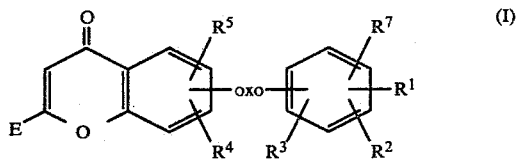

wherein $R^1$, $R^2$, $R^3$, $R^4$, $R^5$ and $R^7$ each represent a group selected from hydrogen, hydroxy, C1 to 6 alkoxy, C1 to 6 alkoxy substituted by phenyl, C2 to 6 alkanoyl, C3 to 6 alkenoyl, amino, C2 to 6 alkanoylamino, C2 to 6 alkenyl, halogen and C1 to 6 alkyl, at least one of $R^1$, $R^2$, $R^3$ and $R^7$ representing a group other than hydrogen and hydroxy, or an adjacent pair of $R^1$, $R^2$, $R^3$ and $R^7$ either represent hydroxy and a 3-(N,N-dialkylamino)acryloyl radical or together represent a chain —COCH═CH—O—, X represents an alkylene chain of 2 to 10 carbon atoms optionally substituted by a hydroxy group, and E represents a carboxy or tetrazole group.

2. A salt according to claim 1 wherein $R^5$ and $R^7$ represent hydrogen, $R^1$ and $R^4$ represent hydrogen, n-propyl or allyl, $R^2$ represents hydroxy, $R^3$ represents acetyl, and X represents a C3 to 7 straight alkylene chain optionally substituted by a hydroxy group.

3. A salt according to claim 1 wherein the compound of formula I is 8-propyl-7-[3-(4-acetyl-3-hydroxy-2-n-propylphenoxy)-2-hydroxypropoxy]-4-oxo-4H-1-benzopyran-2-carboxylic acid.

4. A salt according to claim 1 wherein the compound of formula I is selected from the group consisting of 7-[5-(4-acetyl-3-hydroxyphenoxy)pentyloxy]-4-oxo-4H-1-benzopyran-2-carboxylic acid, 8-Allyl-7-[5-(4-acetyl-2-allyl-3-hydroxyphenoxy)-pentyloxy]-4-oxo-4H-1-benzopyran-2-carboxylic acid, 8-Allyl-7-[5-(4-acetylphenoxy)pentyloxy]-4-oxo-4H-1-benzopyran-2-carboxylic acid, 8-Allyl-7-[5-(2-acetyl-3-hydroxyphenoxy)pentyloxy]-4-oxo-4H-1-benzopyran-2-carboxylic acid, 8-Allyl-7-[5-(4-acetylaminophenoxy)pentyloxy]-4-oxo-4H-1-benzopyran-2-carboxylic acid, 7-[5-(4-Acetylphenoxy)pentyloxy]-4-oxo-4H-1-benzopyran-2-carboxylic acid, 7-[5-(3-Methoxyphenoxy)pentyloxy]-4-oxo-4H-1-benzopyran-2-carboxylic acid, 7-[5-(3-Benzyloxyphenoxy)pentyloxy]-4-oxo-4H-1-benzopyran-2-carboxylic acid, 7-[5-(2-Acetyl-4-allyl-3-hydroxyphenoxy)pentyloxy]-4-oxo-4H-1-benzopyran-2-carboxylic acid, 4-Oxo-7-[5-(2-propylphenoxy)pentyloxy]-4H-1-benzopyran-2-carboxylic acid, 7-[5-(2-t-Butylphenoxy)pentyloxy]-4-oxo-4H-1-benzopyran-2-carboxylic acid, 8-Allyl-7-[3-(4-acetyl-2-allyl-3-hydroxyphenoxy)-2-hydroxypropoxy]-4-oxo-4H-1-benxopyran-2-carboxylic acid, 7-[3-(4-Acetyl-3-hydroxyphenoxy)-2-hydroxypropoxy]-4-oxo-4H-1-benzopyran-2-carboxylic acid, 8-Allyl-7-[3-(4-acetyl-3-hydroxyphenoxy)-2-hydroxypropoxy]-4-oxo-4H-1-benzopyran-2-carboxylic acid, 7-[3-(4-Acetyl-3-hydroxy-2-allylphenoxy)-2-hydroxypropoxy]-4-oxo-4H-1-benzopyran-2-carboxylic acid, 8-Propyl-7-[3-(4-acetyl-3-hydroxy-2-n-propylphenoxy)-2-hydroxypropoxy]-4-oxo-4H-1-benzopyran-2-carboxylic acid, 4-oxo-8-propyl-7-[3-(2-propylphenoxy)-2-hydroxypropoxy]-4H-1-benzopyran-2-carboxylic acid, 4-Oxo-7-[3-(2-propylphenoxy)-2-hydroxypropoxy]-4H-1-benzopyran-2-carboxylic acid, 7-[3-(2-Allylphenoxy)-2-hydroxypropoxy]-4-oxo-4H-1-benzopyran-2-carboxylic acid, 7-[3-(4-Acetyl-3-hydroxy-2-propylphenoxy)-2-hydroxypropoxy]-4-oxo-4H-1-benzopyran-2-carboxylic acid, 7-[3-(4-Acetyl-3-hydroxy-2-propylphenoxy)-2-hydroxypropoxy]-4-oxo-6-propyl-4H-1-benzopyran-2-carboxylic acid, 4-Oxo-6-propyl-7-[3-(2-propylphenoxy)-2-hydroxypropoxy]-4H-1-benzopyran-2-carboxylic acid, 7-[2-Hydroxy-3-(2,4-dimethylphenoxy)propoxy]-4-oxo-4H-1-benzopyran-2-carboxylic acid, 7-[3-(2,4-Di-t-butylphenoxy)-2-hydroxypropoxy]-4-oxo-4H-1-benzopyran-2-carboxylic acid, 7-(3-[2-t-Butylphenoxy]-2-hydroxypropoxy)-4-oxo-4H-1-benzopyran-2-carboxylic acid, 7-[5-(4-Oxo-4H-1-benzopyran-7-yloxy)pentyloxy]-4-oxo-4H-1-benzopyran-2-carboxylic acid, 7-[3-(4-Oxo-4H-1-benzopyran-7-yloxy)-2-hydroxypropoxy]-4-oxo-4H-1-benzopyran-2-carboxylic acid, 7-[3-(4-Acetyl-3-hydroxy-2-propylphenoxy)propoxy]-4-oxo-8-propyl-4H-1-benzopyran-2-carboxylic acid, 4-Oxo-8-propyl-7-[3-(2-propylphenoxy)propoxy]-4H-1-benzopyran-2-carboxylic acid, 4-Oxo-6-propyl-7-[3-(2-propylphenoxy)propoxy]-4H-1-benzopyran-2-carboxylic acid, 8-(3-[2-t-Butylphenoxy]-2-hydroxypropoxy)-4-oxo-4H-1-benzopyran-2-carboxylic acid, 8-[2-Hydroxy-3-(2-iodophenoxy)propoxy]-4-oxo-4H-1-benzopyran-2-carboxylic acid, 8-[3-(2-n-butylphenoxy)-2-hydroxypropoxy]-4-oxo-4H-1-benzopyran-2-carboxylic acid, 8-[2-Hydroxy-3-(2-propylphenoxy)propoxy]-4-oxo-4H-1-benzopyran-2-carboxylic acid, 8-(3-[2-n-butylphenoxy]propoxy)-4-oxo-4H-1-benzopyran-2-carboxylic acid, 4-Oxo-8-[7-(2-n-propylphenoxy)heptyloxy]-4H-1-benzopyran-2-carboxylic acid, 4-Oxo-7-[7-(2-n-propylphenoxy)heptyloxy]-4H-1-benzopyran-2-carboxylic acid, 6-[2-Hydroxy-3-(2-propylphenoxy)propoxy]-4-oxo-4H-1-benzopyran-2-carboxylic acid, 5-[2-Hydroxy-3-(2-propylphenoxy)propoxy]-4-oxo-4H-1-benzopyran-2-carboxylic acid, 4-Oxo-7-(3-[2-propylphenoxy]propoxy)-4H-1-benzopyran-2-carboxylic acid, 5-(4-Oxo-7-[3-(2-propylphenoxy)-propoxy]-4H-1-benzopyran-2-yl)tetrazole, 8-Ethyl-4-oxo-7-(3-[2-propylphenoxy]propoxy)-4H-1-benzopyran-2-carboxylic acid, 5-(3-[2-Acetyl-3-hydroxyphenoxy]-2-hydroxypropoxy)-4-oxo-4H-1-benzopyran-2-carboxylic acid, 5-(3-[4-oxo-1-benzopyran-5-yloxy]-2-hydroxypropoxy)-4-oxo-4H-1-benzopyran-2-carboxylic acid, and 5-(3-[2-(3-dimethylaminoacryloyl)-3-hydroxyphenoxy]-2-hydroxypropoxy)-4-oxo-4H-1-benzopyran-2-carboxylic acid.

5. The lysine salt of 8-propyl-7-[3-(4-acetyl-3-hydroxy-2-n-propylphenoxy)-2-hydroxypropoxy]-4-oxo-4H-1-benzopyran-2-carboxylic acid.

* * * * *

UNITED STATES PATENT AND TRADEMARK OFFICE
CERTIFICATE OF CORRECTION

PATENT NO. : 4,213,903
DATED : July 22, 1980
INVENTOR(S) : JOHN R. BANTICK ET AL.

It is certified that error appears in the above-identified patent and that said Letters Patent are hereby corrected as shown below:

Col. 2, line 59, "bnzopyran", should be --benzopyran--.

Col. 3, line 46, "2-benzopyran-2-carboxylic" should be --2-carboxylic--.

Col. 3, line 55, "dimethylaminocryloyl", should be --dimethylaminoacryloyl--.

Col. 3, line 68, "and and", should be --and arginine and--.

Signed and Sealed this

Third Day of February 1981

[SEAL]

Attest:

Attesting Officer

RENE D. TEGTMEYER

Acting Commissioner of Patents and Trademarks